US008993337B2

(12) United States Patent
Evtodienko et al.

(10) Patent No.: US 8,993,337 B2
(45) Date of Patent: Mar. 31, 2015

(54) REAGENT FOR DETECTION AND ASSESSMENT OF TOTAL CHLORINE IN AQUEOUS SOLUTION

(71) Applicant: LaMotte Chemical Products Company, Chestertown, MD (US)

(72) Inventors: Vladimir Evtodienko, Ottawa (CA); Lydia Kimble Johnson, Chestertown, MD (US)

(*) Notice: Subject to any disclaimer, the term of this patent is extended or adjusted under 35 U.S.C. 154(b) by 236 days.

(21) Appl. No.: 13/853,888

(22) Filed: Mar. 29, 2013

(65) Prior Publication Data

US 2014/0295568 A1    Oct. 2, 2014

(51) Int. Cl.
*G01N 31/22* (2006.01)
*G01N 33/18* (2006.01)
*G01N 21/78* (2006.01)

(52) U.S. Cl.
CPC .............. *G01N 31/22* (2013.01); *G01N 31/224* (2013.01); *G01N 33/182* (2013.01); *G01N 21/78* (2013.01)
USPC .......................................... 436/125; 436/124

(58) Field of Classification Search
CPC ..... G01N 31/22; G01N 21/78; G01N 33/182; G01N 31/224
USPC ................................................. 436/124–125
See application file for complete search history.

(56) References Cited

U.S. PATENT DOCUMENTS

| 4,275,031 | A | 6/1981 | Fischer et al. |
| 5,976,823 | A | 11/1999 | Wu |
| 7,333,194 | B2 | 2/2008 | Jaunakais et al. |
| 7,490,546 | B2 | 2/2009 | Yamashita |
| 2006/0073603 | A1 | 4/2006 | Jaunakais |
| 2014/0295569 | A1* | 10/2014 | Evtodienko et al. .......... 436/125 |

FOREIGN PATENT DOCUMENTS

| CN | 102128833 A | 7/2011 |
| WO | 2011100789 A1 | 8/2011 |

OTHER PUBLICATIONS

Zarei, A. R. et al, Journal of Analytical Chemistry 2011, 66, 269-274.*
European Search Report and Search Opinion for EP14162111, dated Jun. 26, 2014, 6 pages.

* cited by examiner

*Primary Examiner* — Arlen Soderquist
(74) *Attorney, Agent, or Firm* — Drinker Biddle & Reath LLP

(57) ABSTRACT

Provided is a heat dried reagent composition that is dry, methods of making it, and methods of using it. The heat dried reagent composition can be characterized by one or more of: stability to the heat drying conditions; storage stability of the heat dried reagent composition; fast rehydration time; rapid assay kinetics; and assay precision. The reagent composition is useful for detecting and/or assessing total chlorine in an aqueous sample, such as pool water.

20 Claims, 7 Drawing Sheets

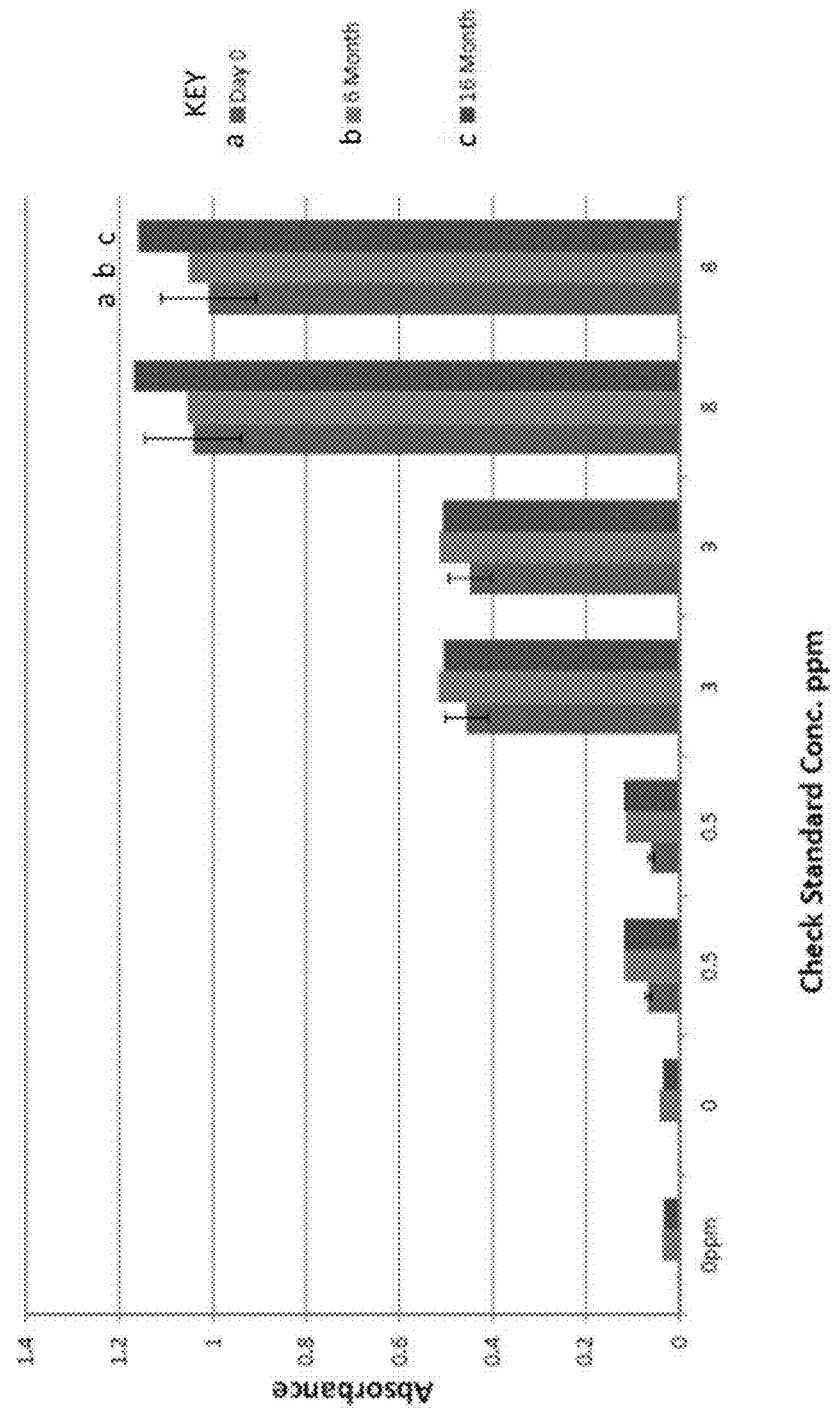

REAGENT FOR DETECTION AND ASSESSMENT OF TOTAL CHLORINE IN AQUEOUS SOLUTION

FIELD OF THE INVENTION

The invention relates to a composition useful for detecting and/or assessing total chlorine in an aqueous sample.

BACKGROUND

In the discussion of the background that follows, reference is made to certain structures and/or methods. However, the following references should not be construed as an admission that these structures and/or methods constitute prior art. Applicants expressly reserve the right to demonstrate that such structures and/or methods do not qualify as prior art.

It is frequently desired to analyze a liquid to determine the presence and concentration of analytes such as minor constituents and/or contaminants. For instance, swimming pool water is tested frequently for various parameters, including alkalinity, pH, chlorine content, bromine content, water hardness and cyanuric acid, in order to maintain safe water for swimmers.

Chlorine is a disinfectant and an oxidizer. As a disinfectant, chlorine can kill bacteria and other microorganisms and helps control algae growth. Chlorine also oxidizes organic matter that might otherwise provide nutrients for microorganism growth. Oxidation of inorganic materials, pyrogens and metals by chlorine helps minimize staining and corrosion. Chlorine is the most widely used chemical for sanitizing and oxidizing pool water and spa water.

Chlorine in pool and spa water can be present in two forms. Free chlorine functions to kill microorganisms such as bacteria, and oxide contaminants. When free chlorine reacts with contaminants, it becomes combined chlorine. Combined chlorine has very little sanitizing ability and no oxidizing ability in pool or spa water. In addition, combined chlorine such as chloramines may cause eye irritation and may produce a chlorine odor that is unpleasant. Therefore, it is important to maintain a sufficient level of free chlorine for sanitization and oxidation in pool or spa water. It is also important to monitor the amount of combined chlorine to manage its presence appropriately.

Maintaining the appropriate level of free chlorine requires testing for free chlorine and total chlorine in pool water. Combined chlorine is calculated as the difference between total chlorine and free chlorine.

Current test kits for testing swimming pool water conventionally require the user to perform one test at a time, which can be time-consuming. Some currently available test kits use reagent solutions that are not stable or utilize a two-part reagent method. Other kits utilize tablets however the rate and complete dissolution of the tablets is problematic. An alternative type of kit utilizes test strips and test strip readers. Strip readers are fast and allow analysis of multiple analytes. However, they are far less accurate than conventional photometric analysis.

One of the most efficient kits currently available is WATERLINK™ 3 EXPRESS, manufactured by LaMotte Company (Chestertown, Md.). This is an in-store pool test system that comprises unit dose vials (UDV). Each vial contains a powdered reagent for a single parameter assessment. Activation of the UDV vials by addition of a sample of pool water is a manual process and is therefore vulnerable to potential operator error. Since multiple UDVs (containing different reagents) are necessary to assess various pool parameters, the testing process can be time consuming. In addition, manufacture of the UDV vials requires dry powdered reagents to be dispensed in each vial in the milligram range. Maintaining the uniformity of a dry powered reagent mixture can be difficult.

There is a need in the art for improved compositions to test an aqueous sample for total chlorine content.

SUMMARY OF THE INVENTION

The following summary is not an extensive overview. It is intended to neither identify key or critical elements of the various embodiments, not delineate the scope of them.

The invention provides a heat dried reagent composition for use in detecting and/or assessing total chlorine in an aqueous solution. The composition comprises: i) an indicator comprising N,N-diethyl-p-phenylenediamine (DPD) in an amount sufficient to detect and/or assess 0.01 to 20 parts per million (ppm) total chlorine in an aqueous reaction solution; ii) a source of iodide; iii) an anionic or nonionic surfactant; iv) ethylenediaminetetraacetic acid (EDTA); and v) a pH 6 buffer in an amount sufficient to obtain a pH of 3.5 to 7.5 in the aqueous reaction solution; wherein the composition is dry.

In an embodiment, the heat dried reagent composition comprises: i) DPD in an amount that will result in 10 parts per million (ppm) to 1000 ppm in an aqueous reaction solution; ii) the source of iodide in an amount that will result in 200 ppm to 7000 ppm in the aqueous reaction solution; iii) the surfactant in an amount that will result in 30 ppm to 600 ppm in the aqueous reaction solution; iv) ethylenediaminetetraacetic acid (EDTA) in an amount that will result in 24 ppm to 960 ppm in the aqueous reaction solution; and v) the pH 6 buffer in an amount that will result in a 1 mM to 100 mM buffer concentration in the aqueous reaction solution.

In embodiments of the composition, the buffer can be selected from the group consisting of: phosphate-borate; imidazole; bis-tris; citrate; malonic acid; malate; MES; and phosphate. In one embodiment, the buffer is phosphate-borate.

In embodiments of the composition, the surfactant comprises a surfactant selected from the group consisting of: sodium ($C_{14}$-$C_{16}$) olefin sulfonate; isopropylamine dodecylbenzene sulfonated, branched; sodium cholate; sodium dioctyl sulfosuccinate; sodium methyl oleoyl taurate; sodium polyoxyethylene(1) lauryl sulfate; octyl phenol ethoxylate; and any combination thereof. In one embodiment, the surfactant comprises sodium ($C_{14}$-$C_{16}$) olefin sulfonate.

In embodiments of the composition, the source of iodide is potassium iodide.

The invention further provides a method of preparing a heat dried reagent composition for use in detecting and/or assessing total chlorine in an aqueous solution. The method comprises drying a volume of an aqueous reagent precursor solution comprising: i) an indicator comprising N,N-diethyl-p-phenylenediamine (DPD) in an amount sufficient to detect and/or assess 0.01 to 20 parts per million (ppm) total chlorine in an aqueous reaction solution; ii) a source of iodide; iii) a pH 6 buffer in an amount sufficient to obtain a pH of 3.5 to 7.5 in the aqueous reaction solution; iv) an anionic or nonionic surfactant; and v) thylenediaminetetraacetic acid (EDTA); wherein the drying is performed at a temperature from about 50° C. to about 105° C. for a sufficient time to obtain a dry composition. The aqueous reagent precursor solution can be about 5 to 30 fold more concentrated than the concentration of the aqueous reaction solution.

In embodiments of the method, the volume of the aqueous reagent precursor solution can be from about 5 microliters to about 150 microliters.

In aspects of the method, the drying is performed at a temperature from about 70° C. to about 95° C. In an embodiment, the volume of the aqueous reagent precursor solution is from about 5 microliters to about 50 microliters.

The method in some embodiments can further comprise, prior to the drying step, the step of aliquoting the aqueous reagent precursor solution into an analysis chamber of a device comprising as least one such chamber.

In an embodiment of the method of preparing a heat dried reagent composition, the heat dried reagent composition comprises: i) DPD in an amount that will result in 10 parts per million (ppm) to 1000 ppm in an aqueous reaction solution; ii) the source of iodide in an amount that will result in 200 ppm to 7000 ppm in the aqueous reaction solution; iii) the surfactant in an amount that will result in 30 ppm to 600 ppm in the aqueous reaction solution; iv) ethylenediaminetetraacetic acid (EDTA) in an amount that will result in 24 ppm to 960 ppm in the aqueous reaction solution; and v) the pH 6 buffer in an amount that will result in a 1 mM to 100 mM buffer concentration in the aqueous reaction solution. The aqueous reagent precursor solution can be about 5 to 30 fold more concentrated than the concentration of the aqueous reaction solution.

The invention further provides a method of assessing total chlorine in an aqueous sample. The method comprises combining an aqueous sample of interest with a heat dried reagent composition of the invention to form a reaction solution; measuring light absorbance of the reaction solution at a wavelength between 490 to 555 nanometers; and converting the light absorbance measurement to a total chlorine amount using a standard curve.

In embodiments of the method, the heat dried reagent composition is present in an analysis chamber of a device comprising at least one such chamber, and the aqueous sample of interest is introduced into the analysis chamber comprising the composition to form the reaction solution.

In embodiments, the light absorbance can be measured within 20 to 60 seconds after the formation of the reaction solution.

In embodiments, the light absorbance is measured at a wavelength between 490 nm to 530 nm.

In embodiments, the aqueous sample of interest is added to the heat dried reagent composition to form the reaction solution having a final volume of 40 microliters to 1 milliliter.

The invention further provides a method of detecting total chlorine in an aqueous sample. The method comprises combining an aqueous sample of interest with a heat dried reagent composition of the invention to form a reaction solution, and observing the color of the reaction solution. A pink color in the reaction solution is indicative of total chlorine in the aqueous sample of interest.

In embodiments of the methods of the invention, the buffer can be selected from the group consisting of: phosphate-borate; imidazole; bis-tris; citrate; malonic acid; malate; MES; and phosphate. In one embodiment, the buffer is phosphate-borate.

In embodiments of the methods of the invention, the surfactant comprises a surfactant selected from the group consisting of: sodium ($C_{14}$-$C_{16}$) olefin sulfonate; isopropylamine dodecylbenzene sulfonated, branched; sodium cholate; sodium dioctyl sulfosuccinate; sodium methyl oleoyl taurate; sodium polyoxyethylene(1) lauryl sulfate; octyl phenol ethoxylate; and any combination thereof. In one embodiment, the surfactant comprises sodium ($C_{14}$-$C_{16}$) olefin sulfonate.

In embodiments of the methods of the invention, the source of iodide is potassium iodide.

BRIEF DESCRIPTION OF THE DRAWINGS

For the purpose of illustrating the compositions and methods disclosed herein, there are depicted in the drawings certain embodiments. However, the compositions and methods are not limited to the precise arrangements and instrumentalities of the embodiments depicted in the drawings.

FIG. 7 depicts representative shelf life data for an exemplary heat dried reagent composition comprising sodium ($C_{14}$-$C_{16}$) olefin sulfonate. From left to right, the set of bars for each chlorine concentration depicted represent time points as follows: a: Day 0; b: 6 Month; and c: 8 Month.

DEFINITIONS

Figure 1:
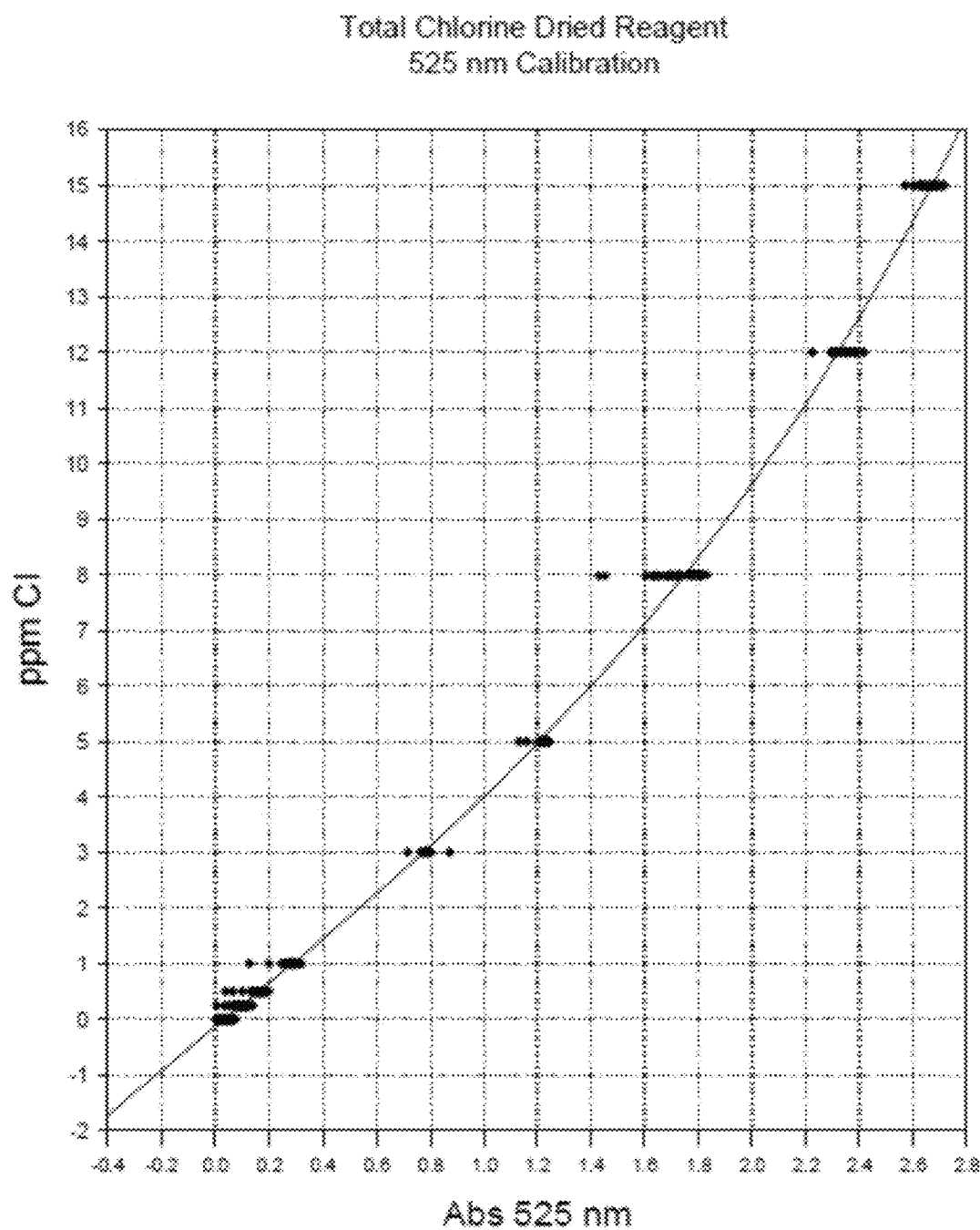
FIG. 1 depicts a graph of absorbance at 525 nm as a function of total chlorine concentration (ppm). The data were prepared using an exemplary heat dried reagent composition of the invention.

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent depending on the context in which it is used. As used herein, "about" is meant to encompass variations of ±20%, more preferably ±10%, more preferably ±5%, even more preferably +1%, and still more preferably +0.1%.

As used herein, "free chlorine" refers to chlorine present in an aqueous solution as aqueous molecular chlorine, hypochlorous acid (HOCl) and/or hypochlorite ion (OCT). Free chlorine is chlorine that has not reacted with foreign substances other than water and is, therefore, available to disinfect the aqueous solution and oxidize organic substances.

As used herein, "total chlorine" refers to the sum of free chlorine and combined chlorine in an aqueous solution.

As used herein, "combined chlorine" refers to the sum of chlorine present in the form of chloramines, including monochloramine ($NH_2Cl$), dichloramine ($NHCl_2$), and nitrogen trichloride ($NCl_3$). Other organic nitrogen compounds, such as amino acids, can also contribute to combined chlorine. To ascertain the combined chlorine level, the free chlorine and total chlorine must be ascertained first. Combined chlorine is then calculated using the following equation:

$$\text{Combined chlorine} = \text{Total chlorine} - \text{Free chlorine} \quad (1)$$

As used herein, "detecting total chlorine" refers to determining the presence or absence of free chlorine in an aqueous sample.

As used herein, "assessing total chlorine" refers to determining the concentration of total chlorine in an aqueous sample.

As used herein, "heat drying" refers to the process of removing water from an aqueous solution by exposing the aqueous solution to heat to obtain a composition with reduced water content. Heat drying can result is a dry composition. A "heat dried composition" refers to a composition that has been subjected to heat drying.

As used herein, "reaction solution" refers to an aqueous solution comprising the rehydrated heat dried reagent composition and the aqueous sample to be tested and in which the total chlorine is intended to be detected and/or assessed. The "final volume" of the reaction solution is the intended volume in which the reaction is carried out and the results of the chlorine assay determined.

The term "dry," as used herein, means a material which contains very little residual water. Residual water refers to the sum of free water, adsorbed water, and water of crystallization. As used herein, "very little residual water" refers to less than 4% residual water and preferably, less than about 1% residual water.

The term "anhydrous," as used herein, means a material that does not contain residual water. An anhydrous material is also dry, as defined above. However, a dry material is not necessarily anhydrous, as defined herein.

The term "pH 6 buffer" as used herein refers to a buffer that has a buffering capacity in an aqueous solution within the range of pH 3.5 to 8, pH 4.5 to 7.5, or pH 4.5 to 7.0. The buffering capacity of a pH 6 buffer can exceed these ranges but must include a pH range overlapping or within this pH range to be deemed a pH 6 buffer. For instance, a buffer having a buffering range of pH 3 to pH 5.5 is deemed a pH 6 buffer.

As used herein, "storage stabile" or "storage stability" with regard to the dried reagent composition of the invention refers to a composition that has been stored for a period time and retains substantially the same rehydration kinetics, assay kinetics, and/or assay detection range and precision as a composition that has been freshly prepared and heat dried. In this context, "substantially the same" means the value obtained with a stored heat dried reagent composition is within 15%, 12.5%, 10%, 9%, 8%, 7%, 6%, or 5% of the value obtained using the same composition that has been freshly prepared and heat dried. In an embodiment, a composition is considered storage stable if there is no more than a 10% change in absorbance value over the full analyte concentration range within 12 weeks of storage at 38° C., wherein the composition is stored with a desiccant in a sealed container. A full analyte concentration range can be, for instance, 0.5 ppm, 3 ppm and 8 ppm free chlorine.

All percents, parts, and ratios herein are by weight unless specifically noted otherwise.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

It is understood that any and all whole or partial integers between any ranges set forth herein are included herein.

DETAILED DESCRIPTION

The invention provides a heat dried reagent composition that possesses improved properties including, but not limited to: stability of the components to the heat drying condition used to prepare the heat dried composition from an aqueous reagent precursor solution; storage stability of the heat dried reagent composition; fast rehydration time; rapid assay kinetics; and assay precision. The composition of the invention is useful for rapid, visual or photometric detection and/or photometric assessment of total chlorine in an aqueous solution. The composition is particularly suitable for use in small scale (e.g., less than 1 ml sample size) photometric detection and/or assessment methods and/or systems. Small scale systems utilize smaller amounts of material, which provides an economic advantage and may also produce less waste, which is also advantageous.

The heat dried reagent composition of the invention can be obtained by heat drying a reagent precursor solution comprising the components of the reagent composition. A benefit of the components of the reagent composition is that the reagent precursor solution comprising the components can be heat dried without damaging the chemical/functional integrity of the components. Additionally, the heat dried reagent composition of the invention is expected to have a long shelf life. For instance, in accelerated stability experiments, an exemplary heat dried reagent composition of the invention stored at 38° C. for 12 weeks, or at 55° C. for 12 weeks, exhibited storage stability. Moreover, shelf life experiments at room temperature for the exemplary heat dried reagent composition confirmed storage stability at 6 and 16 months. Thus, the heat dried reagent composition of the invention can have a shelf life of at least about 4 months, at least about 6 months, at least about 8 months, at least about 16 months or more. In an embodiment, the shelf life of the heat dried reagent composition is from about 16 months to 2 years, or more.

The heat dried reagent composition of the invention can be rapidly rehydrated for use in detecting and/or assessing total chlorine. The heat dried reagent composition can be fully rehydrated within about 60 seconds, 55 seconds, 50 seconds, 45 seconds, 40 seconds, 35 seconds, 30 seconds, 25 seconds, 20 seconds, 15 seconds, or about 10 seconds. In a preferred embodiment, the heat dried reagent composition can be rehydrated within about 10 to 20 seconds. Advantageously, rehydration of the heat dried reagent composition does not require intensive agitation.

The rehydrated reagent composition exhibits fast total chlorine assay kinetics. As used herein, "fast assay kinetics" refers to the DPD reaction for pool water reaching an absorbance plateau that is sustained for at least about 10 to 20 seconds at room temperature within about 60 seconds, about 50 seconds, about 40 seconds, about 35 seconds, or about 20 seconds, or less. In an embodiment, the DPD assay for total chlorine (wherein the combined chlorine is mono-, di- and tri-chloramines) in pool water reaches an absorbance plateau within about 15 to 35 seconds, about 15 to 30 seconds, about 20 to 35 seconds, or about 20 to 30 seconds. Assay kinetics for detecting total chlorine in other aqueous samples comprising a larger amount of combined chlorine other than mono-, di- and tri-chloramines may require a longer period of time to reach an absorbance plateau, due to the slower reaction kinetics of KI with the combined chlorine. Thus, in the context of detecting total chlorine in, for instance, waste water, "fast assay kinetics" refers to the DPD reaction reaching an absorbance plateau at room temperature within about 2 minutes.

I. Components of the Composition

The heat dried reagent composition of the invention comprises indicator (I), surfactant (S), EDTA (E), an iodide (D), and buffer (B). In some embodiments in the following discussion, the amount of each component in the heat dried reagent composition is described with regard to the desired concentration of that component in the reaction solution.

With regard to surfactants in solution, S refers to the weight of the active component. For instance, BIO TERGE® AS 40 (Stepan Company, Northfield, Ill.) is available as an aqueous solution comprising 39.1% actives. Thus, S for BIO TERGE® AS 40 refers to the weight of the actives and does not, for instance, include the weight of the water. For instance, a stock solution of 15% BIO TERGE® AS 40 comprises 5.86% actives. Fifty (50) milliliters of the 15% solution therefore contains a total of 2.93 milligrams actives.

IA. Indicator (I)

The indicator in the dry reagent composition comprises N,N-diethyl-p-phenylenediamine (DPD).

In experiments pursued to develop the reagent composition of the invention, syringaldazine (SAZ) was tested as a possible indicator because it is known to have better storage stability compared to DPD. However, it was discovered that a heat dried composition comprising SAZ could only be rehydrated in water using LUVIQUAT® Mono LS (BASF, Florham Park, N.J.) additive. However, LUVIQUAT® Mono LS was also found to cause precipitation of the components in solution. Moreover, rehydration of a heat dried composition comprising SAZ also required very intensive mixing and for a duration of at least about 20 to 30 seconds. In contrast, a heat dried composition comprising DPD was found to rapidly rehydrate in an aqueous solution and without the need for very intensive mixing. The heat dried reagent composition of the invention comprising DPD was also found to be storage stable. The storage stability of the dry reagent composition of the invention was unexpected as DPD is known to have poorer storage stability compared to SAZ.

Chlorine can oxidize DPD to two oxidation products. The primary oxidation product at about neutral pH is a cationic compound known as a Wurster dye. The Wurster dye is a relative stable free radical species that provides a pink color in the reaction solution. The Wurster dye is the principal oxidation product when DPD reacts with small amounts of chlorine at about neutral pH. At higher oxidant levels, however, DPD can be further oxidized to a relatively unstable, colorless imine compound, that results in the diminution or fading of the pink color in the reaction solution. Thus, it is important to always have an excess of DPD in the composition to obtain an accurate assessment of the total chlorine present.

The amount of DPD present in the heat dried reagent composition can be determined by the desired final concentration of DPD in the reaction solution, and the total volume of reaction solution. The heat dried reagent composition can comprise an amount of DPD sufficient to detect and/or assess total chlorine in an amount ranging from about 0.01 ppm to about 20 ppm total chlorine, or from about 0.05 ppm to about 20 ppm total chlorine in the final volume of the reaction solution. The heat dried reagent composition can comprise an amount of DPD such that the final DPD concentration in the reaction solution is about 10 parts per million (ppm) to about 1000 ppm, or about 10 ppm to about 600 ppm. As used herein, ppm refers to the mass ratio of a component to the reaction solution (assumed herein to have a density of 1 g/ml). For detecting from 0.01 to 20 ppm total chlorine in the reaction solution, a preferred DPD concentration in the reaction solution is from about 200 ppm to 400 ppm, or 240 ppm to 360 ppm. For detecting from 0.01 to 1 ppm total chlorine in the reaction solution, a preferred DPD concentration in the reaction solution is from about 10 ppm to 100 ppm, or 20 ppm to 30 ppm.

IB. Iodide (D)

Total chlorine is the sum of free chlorine and combined chlorine. Free chlorine reacts with DPD directly to form the Wurster dye. However, at near neutral pH, combined chlorine species (e.g., chloramines) are slow to react directly with DPD. In order to detect and/or assess these species, an iodide source, such as potassium iodide, is part of the composition. Chloramines oxidize the iodide to iodine (as the triiodide ion $I_3^-$). The liberated iodine ($I_3^-$) then reacts with DPD to form the Wurster dye.

The source of iodide in the heat dried reagent composition generally can be any iodide-containing compound that is water soluble and that is not adversely affected by the heat drying conditions for preparing the heat dried reagent composition. Preferred sources of iodide are iodide salts, and in particular, potassium iodide and sodium iodide. In an embodiment, the source of iodide is potassium iodide.

In an embodiment, the heat dried reagent composition comprises an amount of potassium iodide such that the final potassium iodide concentration in the reaction solution is about 200 ppm to 7000 ppm, or about 400 ppm to about 4000 ppm.

IC. Surfactant (S)

The composition comprises a surfactant.

Initial experiments were pursued testing a variety of agents for their effect on composition rehydration and reagent stability regarding the heat-drying process. The agents tested were polymers, including PEG and PVA, and carbohydrates, including dextran, sucrose, lactose, trehalose, and sorbitol. Surfactants were also tested, including TRITON™ X-100 (Dow Chemical, Midland, Mich.), TETRONIC® 1307 (BASF, Florham Park, N.J.), Surfactant 10G, SURFYNOL® 465 (Air Products, Allentown, Pa.), TRITON™ X-305, sodium cholate, and BIO TERGE® AS-40 (Stepan Company, Northfield, Ill.). None of the polymers or carbohydrates tested contributed positively to the rate of heat dried composition rehydration. Some of the surfactants (TRITON™ X-100, SURFYNOL® 465 and BIO TERGE® AS 40), however, were found to contribute positively to the rate of dried composition rehydration.

Surfactants were also tested for their effect on the storage stability of the heat dried composition. An accelerated stability study (stability studied under conditions designed to predict shelf life) on heat dried compositions comprising TRITON™ X-100, SURFYNOL® 465, or BIO TERGE® AS 40 was performed. A heat-dried composition comprising BIO TERGE® AS 40, an anionic surfactant, was found to have the most favorable storage stability compared to TRITON™ X-100 and SURFYNOL® 465.

Without wishing to be limited by theory, DPD oxidation is believed to cause coloration of the heat dried reagent composition during storage of the heat dried composition. Coloration of the heat dried reagent composition can cause an increase in background color in the reaction solution, and a reduction in the signal in the reaction solution, which are problematic for precision and accuracy of testing for total chlorine. Antioxidants such as tocopherol, BHT and ascorbic acid were tested for the capacity to minimize or preclude DPD oxidation in the heat dried reagent composition during storage, but were found to be not effective. Advantageously, TRITON™ X-100, SURFYNOL® 465, and BIO TERGE® AS 40 were found to minimize or preclude DPD degradation and coloration during storage, thereby contributing to storage stability The surfactant in the heat dried reagent composition of the invention is preferably an anionic or nonionic surfactant. Anionic surfactants useful in the composition include, but are not limited to: sodium ($C_{14}$-$C_{16}$) olefin sulfonate (CAS number 7732-18-5); isopropylamine dodecylbenzene sulfonated, branched (CAS number 157966-96-60; sodium cholate; sodium dioctyl sulfosuccinate (CAS number 577-11-7); sodium methyl oleoyl taurate (CAS number 137-20-2); and sodium polyoxyethylene(1) lauryl sulfate (CAS number 68585-34-2). A nonionic surfactant useful in the composition includes, but is not limited to, octyl phenol ethoxylate (CAS number 9002-93-1). Combinations of any of these surfactants are also contemplated in the composition. In an embodiment, the surfactant comprises one of sodium ($C_{14}$-$C_{16}$) olefin sulfonate, and octyl phenol ethoxylate. In an embodiment, the surfactant comprises sodium ($C_{14}$-$C_{16}$) olefin sulfonate.

Sodium ($C_{14}$-$C_{16}$) olefin sulfonate (MW 315) is commercially available as BIO-TERGE® AS-40 from Stepan Company (Northfield, Ill.). Isopropylamine dodecylbenzene sulfonated, branched, MW 385 (also referred to as benzenesulfonic acid, (tetrapropenyl)-, compound with 2-propanamine (1:1)) is commercially available as NINATE® 411 (Stepan Company, Mexico). Sodium cholate (MW 431; as referred to as 3,7,12-trihydroxy-5β-cholan-24-oic acid, monosodium salt) is commercially available from a number of vendors. Sodium dioctyl sulfosuccinate (MW 444) is commercially available as AEROSOL® OT-100 (Cytec Industries Inc., West Paterson, N.J.). Sodium 2-[methyloleoylamino]ethane-1-sulphonate (MW 425; also referred to as sodium methyl oleoyl taurate) is commercially available as GEROPON T 77 (Solvay-Rhodia, Italy). Sodium polyoxyethylene(1) lauryl sulfate (MW 346; also referred to as sodium laureth sulfate) is commercially available as STANDAPOL® ES-1 (BASF, Florham Park, N.J.). Octyl phenol ethoxylate (MW 624; also known at TRIFON X-100) is commercially available from J. T. Baker.

In an embodiment, the heat dried reagent composition comprises an amount of surfactant such that the final surfactant concentration in the reaction solution is about 30 ppm to 600 ppm, or about 240 ppm to about 360 ppm.

ID. Stabilizer-EDTA (E)

The composition comprises ethylenediaminetetraacetic acid (EDTA). While not wishing to be limited to theory, it is believed the EDTA contributes to the stability and/or performance properties of the dried reagent composition by acting as an interference scavenger.

In an embodiment, the heat dried reagent composition comprises an amount of EDTA such that the final EDTA concentration in the reaction solution is about 24 ppm to 960 ppm, or about 120 ppm to about 480 ppm.

IE. Buffer

The composition comprises a pH 6 buffer. Initial experiments on dried compositions comprising different buffers were performed. The effect of the buffer on rehydration of the dried composition was assessed. Buffers with very good rehydration rate include citrate, bis-tris, and malonic acid. Buffers discovered to have excellent rehydration rate of the heat-dried reagent composition include phosphate-borate and imidazole.

Buffers useful as a pH 6 buffer in a dried reagent composition of the invention include: phosphate-borate; imidazole; bis-tris; malonic acid; citrate; malate; MES; phosphate; BES; bicine; succinate; PIPES; ADA and maleate. In an embodiment, the buffer is selected from phosphate-borate; imidazole; bis-tris; malonic acid; citrate; malate; MES; and phosphate. In an embodiment, the buffer is phosphate-borate.

The composition comprises the pH 6 buffer in an amount sufficient to obtain a suitable pH in the reaction solution. Buffer concentrations useful in the final reaction solution are from 1 millimolar (mM) to 200 mM. Accordingly, in an embodiment, the heat dried reagent composition comprises an amount of buffer that will result in a 1 mM to 200 mM, 1 mM to 100 mM, 1 mM to 50 mM, or 1 mM to 25 mM buffer concentration in the reaction solution. In an embodiment, the buffer is present in the dried reagent composition in an amount sufficient to result in about a 5 mM to 15 mM concentration in the reaction solution.

A suitable pH for the reaction solution comprising the reagent composition of the invention is a pH of 3.5 to 7.5, a pH of 4.5 to 6.7, a pH of 6.2 to 6.5, or a pH of 6.1 to 6.3. In an embodiment, the buffer is present in an amount sufficient to obtain a pH of about 6.1 to about 6.3 in the final reaction solution. As a general rule, the fewer solids in the dried composition, the better it is for obtaining a rapid rehydration. Therefore, the lowest amount of buffer to obtain the desired pH in the reaction solution is preferred. The ordinarily skilled artisan can readily determine the appropriate amount of buffer for the heat-dried composition in view of the teachings herein and the knowledge in the art.

In an embodiment, the heat dried reagent composition comprises phosphate-borate buffer present in an amount to obtain a pH of 4.5 to 6.7, 6.2 to 6.5, or 6.1 to 6.3 in the reaction solution. In an embodiment, the heat dried reagent composition comprises an amount of phosphate-borate buffer such that the final buffer concentration in the reaction solution is about 148 ppm to 4972 ppm, or about 497 ppm to about 3729 ppm. In an embodiment, the heat dried reagent composition comprises: (i) an amount of $K_2HPO_4$ such that the final $K_2HPO_4$ concentration in the reaction solution is about 243 ppm; (ii) an amount of boric acid such that the final boric acid concentration in the reaction solution is about 111 ppm; and (iii) an amount of $NaH_2PO_4$ such that the final $NaH_2PO_4$ concentration in the reaction solution is about 143 ppm, such that that final phosphate-borate buffer concentration is about 497 ppm. In an embodiment, the heat dried reagent composition comprises: (i) an amount of $K_2HPO_4$ such that the final $K_2HPO_4$ concentration in the reaction solution is about 1822 ppm; (ii) an amount of boric acid such that the final boric acid concentration in the reaction solution is about 831 ppm; and (iii) an amount of $NaH_2PO_4$ such that the final $NaH_2PO_4$ concentration in the reaction solution is about 1076 ppm, such that that final phosphate-borate buffer concentration is about 3729 ppm.

IF. Composition Embodiments

Exemplary compositions of the invention are summarized in Tables 1 and 2. In these tables, the amount listed is the final component concentration desired in the reaction solution comprising a rehydrated heat dried reagent composition. Generally, it is preferably that final surfactant concentration in the reaction solution is directly related to the final DPD concentration. Specifically, for a heat dried reagent composition intended to have a higher final concentration of DPD (within the ranges disclosed) in the reaction solution, the composition should also have a sufficient amount of surfactant to yield a higher final concentration of surfactant (within the ranges disclosed) in the reaction solution.

TABLE 1

| Comp. # | DPD (ppm) | Iodide (ppm) | EDTA (ppm) | Surfactant (ppm) | Buffer (mM) |
|---|---|---|---|---|---|
| 1 | 10-1000 | 200-7000 | 24-960 | 30-600 | 1-200 |
| 2 | 200-600 | 400-4000 | 120-480 | 240-360 | 1-100 |
| 3 | 240-360 | 400-4000 | 24-960 | 240-360 | 1-100 |
| 4 | 20-30 | 400-4000 | 24-960 | 20-120 | 1-100 |

TABLE 2

| Comp. # | DPD (ppm) | Iodide (ppm) | EDTA (ppm) | Surfactant (ppm) | Buffer (ppm) |
|---|---|---|---|---|---|
| 5 | 10-1000 | 200-7000 | 24-960 | 30-600 | 148-4972 |
| 6 | 200-600 | 400-4000 | 120-480 | 240-360 | 497-3729 |
| 7 | 240-36 | 400-4000 | 24-960 | 240-360 | 497-3729 |
| 8 | 20-30 | 400-4000 | 24-960 | 20-120 | 497-3729 |

In the compositions shown in Tables 1 and 2, the buffer is preferably selected from phosphate-borate; imidazole; bistris; malonic acid; citrate; malate; MES; and phosphate; the iodide is potassium iodide; and the surfactant is preferably selected from sodium ($C_{14}$-$C_{16}$) olefin sulfonate, and octyl phenol ethoxylate.

In one aspect, the heat dried reagent composition of the invention comprises phosphate-borate buffer, DPD, potassium iodide, sodium ($C_{14}$-$C_{16}$) olefin sulfonate, and EDTA. Exemplary compositions for this aspect are shown in Table 3. In this table, the amount listed is the final component concentration desired in the reaction solution comprising a rehydrated heat dried reagent composition.

TABLE 3

| Comp. # | DPD (ppm) | KI (ppm) | EDTA (ppm) | sodium ($C_{14}$-$C_{16}$) olefin sulfonate surfactant (ppm) | Phosphate-borate buffer (ppm) |
|---|---|---|---|---|---|
| 9 | 10-1000 | 200-7000 | 24-960 | 30-600 | 148-4972 |
| 10 | 200-600 | 400-4000 | 120-480 | 240-360 | 497-3729 |
| 11 | 240-360 | 400-4000 | 24-960 | 240-360 | 497-3729 |
| 12 | 20-30 | 400-4000 | 24-960 | 20-120 | 497-3729 |

II. Heat Dried Reagent Composition Preparation

The invention further provides a method of preparing the heat dried reagent composition. The method comprises drying a reagent precursor solution under heat. "Reagent precursor solution" refers to an aqueous solution comprising the reagent components in appropriate amounts to result in the desired amount in the final volume of the reaction solution. The reagent precursor is then dried under heat to prepare the heat dried reagent composition.

Prior art powdered reagent formulations for detecting total chlorine are typically prepared by freeze-drying (also called lyophilization) or mixing of dry reagent components. The freeze drying process is necessarily a batch process and cannot be readily incorporated into a continuous production line. Distributing a dry mixture can be challenging to maintain the homogeneity of the mixture and to accurately dispense, particularly in small quantities, the powdered formulation for testing. Heat drying the reagent precursor solution of the present disclosure is advantageous over the prior art methods for at least the following reasons. First, the heat drying step can be readily incorporated into a continuous production line, which is not readily possible for a process using freeze drying. In addition, the homogeneity of the reagent precursor solution of the invention is readily achieved and maintained because it is a solution. The homogenous reagent precursor solution can be distributed into multiple individual containers with a high level of accuracy and then heat dried. The resulting heat dried composition in the multiple containers is characterized in part by reproducible assay results, which, without wishing to be limited by theory, is believed due at least partially to the initial homogeneity of the solution. Without wishing to be limited by theory, the reproducibility of assay results with the dried reagent composition of the invention is also believed due to the rapid and complete rehydration made possible by the heat dried reagent composition of the invention.

The reagent precursor can be dried at a temperature from about 50° C. to about 105° C., from about 60° C. to about 100° C., or from about 70° C. to about 95° C., for a sufficient amount of time to dry the reagent precursor and thereby prepare the heat dried reagent composition, wherein the composition is dry. In an embodiment, the drying results in an anhydrous composition. In an embodiment, the process for preparing the heat dried reagent composition excludes freeze drying. Accordingly, in an embodiment, the heat dried composition of the invention excludes a freeze dried composition. In an embodiment, the heat dried composition excludes a composition prepared by the mixing of dry components.

The reagent precursor solution can be prepared in a large volume batch and then can be aliquoted in an amount that, when rehydrated, is suitable for detection of total chlorine in a reaction solution having a total final volume of from 10 microliters to 3 milliliters (ml). Aliquot size of the reagent precursor solution will be influenced by the maximum concentration possible for the components in the reagent precursor, the length of time needed to heat dry the composition, and the desired final volume of reaction solution. The reagent precursor solution can comprise each component in the same concentration as the desired final reaction solution. Alternatively, in a preferred embodiment, the reagent precursor solution is concentrated relative to the desired reaction solution. This enables a smaller volume of the reagent precursor solution to be aliquoted and dried under heat to prepare the heat dried reagent composition. For instance, if the reagent precursor solution is 10 fold more concentrated than the desired final reaction solution, and the intended final volume of the reaction solution is 200 microliters, then 20 microliters of the reagent precursor solution can be aliquoted and dried under heat to form the heat dried reagent composition.

Aliquot size can be from 2 microliters to 200 microliters, 2 microliters to 50 microliters, 5 microliters to 15 microliters, or 10 microliters to 15 microliters. In a preferred embodiment, the aliquot size is 10 microliters.

In a preferred embodiment, the reagent precursor solution is aliquoted in an amount suitable for detecting and/or assessing total chlorine in the range of about 0.01 ppm to about 20 ppm when the dry reagent composition is rehydrated to an appropriate final volume for the reaction solution. The final volume of the reaction solution can be from about 10 microliters to about 3 ml, from about 40 microliters to about 2 ml, from about 40 microliters to about 1 milliliter (ml) or from about 150 microliters to about 1 ml. In an embodiment, the reagent precursor solution is aliquoted in an amount such that the dried reagent composition is in a 200 microliter final volume of reaction solution for detection and/or assessment of total chlorine.

Each aliquot of reagent precursor solution is dried under heat to prepare the heat dried reagent composition. The drying is carried out until the composition is dry, as defined herein. Aliquots can be dried individually or in small batches. Alternatively, aliquots are dried in a continuous process by means of a drying oven on a production line.

The reagent precursor solution is generally stable (e.g., DPD is no more than minimally oxidized or otherwise degraded) for at least about 24 hours after the reagent precursor is prepared and prior to drying. Optionally, the reagent precursor solution can be prepared and/or stored under a nitrogen atmosphere to prolong the stability of the reagent precursor, prior to drying to form the heat dried reagent composition, wherein the composition is dry.

In an embodiment, the reagent precursor solution is aliquoted into individual containers suitable for carrying out a single reaction, and optionally suitable for photometric analysis. Containers can be single-use or can be reused. Suitable containers include, but are not limited to, glass vials, plastic vials, the lid or cap of a plastic or glass vial, a device such as a cartridge comprising at least one analysis chamber. As used herein an "analysis chamber" refers to a chamber having an opening to admit a aqueous test sample into the chamber, wherein the chamber has sufficient volume for combining the aqueous test sample with the heat dried reagent composition to rehydrate the heat dried reagent composition. The device may comprise two or more analysis chambers, wherein each analysis chamber can comprise the heat dried reagent composition of the invention. This device can be used to test multiple different aqueous samples for total chlorine, or multiple replicate assays on the same aqueous sample. Alternatively, each analysis chamber can comprise a different reagent for detecting a different constituent in an aqueous sample. The reaction solution in the analysis chamber may be analyzed by, for instance, photometry. An example of a cartridge comprising at least one analysis chamber and a photometric system employing the cartridge are described in U.S. patent application Ser. No. 13/611,843 filed Sep. 12, 2012 and entitled "Liquid Analysis Apparatus and Methods", which is incorporated herein by reference in its entirety.

The heat dried reagent composition of the invention is preferably stored in a sealed package with a desiccant or molecular sieve to preserve the dryness of the composition. Preferably, the heat dried reagent composition is stored away from exposure to light. Light impermeable blister packs are a suitable form of storage. The heat dried reagent composition can be stored at room temperature.

III. Heat Dried Reagent Composition Methods of Use

The heat dried reagent composition can be used in any method of detecting and/or assessing total chlorine in an aqueous sample of interest. The aqueous sample of interest can be pool water, spa water, rain water, ground water, drinking water, industrial process water, industrial effluent, sewage, sludge, grey water, spring water, aquifer water, sea water, tap water, irrigation water, agricultural feed water, glacial melt water, treated water, untreated water, steam or atmospheric humidity, or any other aqueous sample of interest. In a preferred embodiment, the aqueous sample of interest is selected from pool water and spa water. In instances where the aqueous sample of interest may comprise a constituent that will adversely impact the accuracy of the total chlorine detection and/or assessment, the heat dried reagent composition can optionally further comprise one or more components to counter the adverse impact.

Generally, the dry reagent composition is rehydrated by addition of the appropriate volume of an aqueous sample to arrive at the final volume of the reaction solution. The aqueous sample is typically at room temperature (about 18° C. to about 25° C.) when combined with the heat dried reagent composition. Advantageously, the heat dried reagent composition of the invention can be rapidly rehydrated upon the addition of an aqueous sample at room temperature. Rehydration can be aided by agitation or aspiration.

In one embodiment, the heat dried reagent composition is first rehydrated by the addition of a volume of water. The rehydrated reagent is then combined with a volume of an aqueous sample to be tested for the presence and/or amount of total chlorine to prepare the final volume of reaction solution. The dilution of the aqueous sample of interest by the initial volume of water can be taken into account in the final assessment of the total chlorine.

In an alternative embodiment, the heat dried reagent composition is rehydrated directly with an appropriate volume of the aqueous sample during the testing to form the reaction solution. For example, the dried reagent composition is included in a compartment of a sample testing cartridge. During testing, a portion of the sample is channeled to the compartment and rehydrates the composition. Testing is then conducted on the rehydrated solution.

In the rehydrated reagent composition, the reaction of total chlorine with iodide to form tri-iodide which then reacts with DPD (N,N-diethyl-p-phenylenediamine) indicator occurs immediately to form a pink color (the Wurster dye). As a qualitative test, the presence of total chlorine is indicated by the presence of a pink color in the reaction solution. The pink color can be observed visually. The reaction solution can be optionally compared to the aqueous sample in the absence of the dry reagent composition and/or to the dry reagent composition rehydrated with water known to contain no total chlorine to confirm the specificity of the pink color presence.

The pink color that forms by the reaction of total chlorine with iodide to form tri-iodide which then reacts with DPD is proportional to the chlorine concentration, when a sufficient amount of indicator is present in the dry reagent composition. Therefore, as a quantitative test, the concentration of total chlorine in the reaction solution can be determined by photometry. The Wurster dye color can be measured photo-metrically at wavelengths ranging from about 490 to about 555 nanometers (nm) or from 490 nm to 530 nm. In a preferred embodiment, the light absorbance of the reaction solution is measured at 525 nm. The light absorbance can be converted to a concentration of total chlorine by comparison to a standard curve of total chlorine in an aqueous solution. The conversion can be done manually or can be done by a computer. The light absorbance of the reaction solution can optionally be normalized relative to the aqueous sample in the absence of the dry reagent composition and/or to the dry reagent composition rehydrated with water known to contain no total chlorine. Thus, the dry reagent composition can be used to assess quantitatively the total chlorine in an aqueous sample of interest.

The kinetics of the reaction of total chlorine with the reagent composition of the invention are rapid. For instance, for a reaction volume of about 50 microliters to about 1 ml, the reaction can reach an absorbance plateau in about 60 seconds or less, about 55 seconds or less, about 50 seconds or less, about 45 seconds or less, about 40 seconds or less, about 35 seconds or less, about 25 seconds or less, or about 15 seconds or less. As discussed elsewhere herein, assay kinetics for detecting total chlorine in aqueous samples comprising a larger amount of combined chlorine other than mono-, di- and tri-chloramines may require a longer period of time to reach an absorbance plateau, due to the slower reaction kinetics of KI with the combined chlorine. In an embodiment, the reaction can reach an absorbance plateau at room temperature within about 2 minutes.

The heat dried reagent composition is suitable for use in individual test vials for in-the-field or in-lab analysis systems such as SMART3 Photometer (LaMotte Company, Chestertown, Md.). The heat dried reagent composition is also suitable for use in an automated photometric system for analyzing pool or spa water samples. An exemplary system is the WaterLink™ Spin analyzer (LaMotte Company, Chestertown, Md.).

The products, methods of their manufacture and methods of use are further described in detail by reference to the following experimental examples. These examples are provided for purposes of illustration only, and are not intended to be limiting unless otherwise specified. Thus, the compositions and methods of use should in no way be construed as being limited to the following examples, but rather, should be construed to encompass any and all variations which become evident as a result of the teaching provided herein.

EXAMPLES

Example 1

A reagent precursor was prepared such that 10 microliters of the reagent precursor, when heat dried to form a heat dried reagent composition, can be rehydrated with aqueous sample of interest to a final volume of 200 microliters and result in a reaction solution having the following composition (not including constituents of the aqueous sample of interest) and a pH of 6.2 to 6.5:

7 mM $K_2HPO_4$
9 mM boric acid
6 mM $NaH_2PO_4$
0.24 mg/ml EDTA
0.0293% sodium ($C_{14}$-$C_{16}$) olefin sulfonate
0.3 mg/ml DPD
2 mg/ml KI Stock solutions of two of the components were prepared as follows.

Phosphate-borate buffer stock: 122 g $K_2HPO_4$; 55.6 g boric acid: and 71.0 g $NaH_2PO_4$ were dissolved in deionized (DI) water to a final volume of 1000 ml. The resulting buffer stock was 0.7 M $K_2HPO_4$; 0.9 M boric acid; and 0.59 M $NaH_2PO_4$ and had a pH of 6.1±0.05.

BIO TERGE® AS-40 stock: 100 g of BIO TERGE® AS-40 (having 39.1% sodium ($C_{14}$-$C_{16}$) olefin sulfonate actives) was combined with 900 ml DW water to prepare a stock solution having 3.91% actives.

To prepare a reagent precursor, the amounts shown in Table 4 were combined to prepare 3000 ml of reagent precursor solution.

TABLE 4

| Component | Amount | Conc. in reagent precursor solution |
|---|---|---|
| Phosphate-borate buffer stock | 600 ml | 0.14M $K_2HPO_4$<br>0.18M boric acid<br>0.12M $NaH_2PO_4$ |

TABLE 4-continued

| Component | Amount | Conc. in reagent precursor solution |
|---|---|---|
| EDTA | 14.4 grams | 4.8 mg/ml |
| BIO TERGE® AS-40 stock | 450 ml | 0.586% actives |
| KI | 120 grams | 40 mg/ml |
| DPD | 18 grams | 6 mg/ml |
| DI water | 1950 ml | n/a |

A 10 microliter aliquot of the reagent precursor solution was dispensed into wells of a microtiter plate. The aliquots are dried for about 15 minutes in a small convection oven at 75° C. to form a heat dried reagent composition.

A 200 microliters aliquot of an aqueous sample of interest can be added to a well for the assay. The liquid can be aspirated up and down to rehydrate the heat dried reagent composition in each well to form the reaction solution. The absorbance of the reaction solution can be read at 525 nm.

The aqueous sample of interest can be a free chlorine standard solution having a known amount of free chlorine. Measuring absorbance for standard solutions having different concentrations of free chlorine can be used to prepare a standard curve.

FIG. 1 depicts an actual standard curve prepared using an exemplary heat dried composition of the invention and a standard chlorine solution. Multiple duplicates were prepare and assayed at each concentration of standard chlorine solution. The absorbance was read at 525 nm.

Example 2

Assay Kinetics

Figure 2:
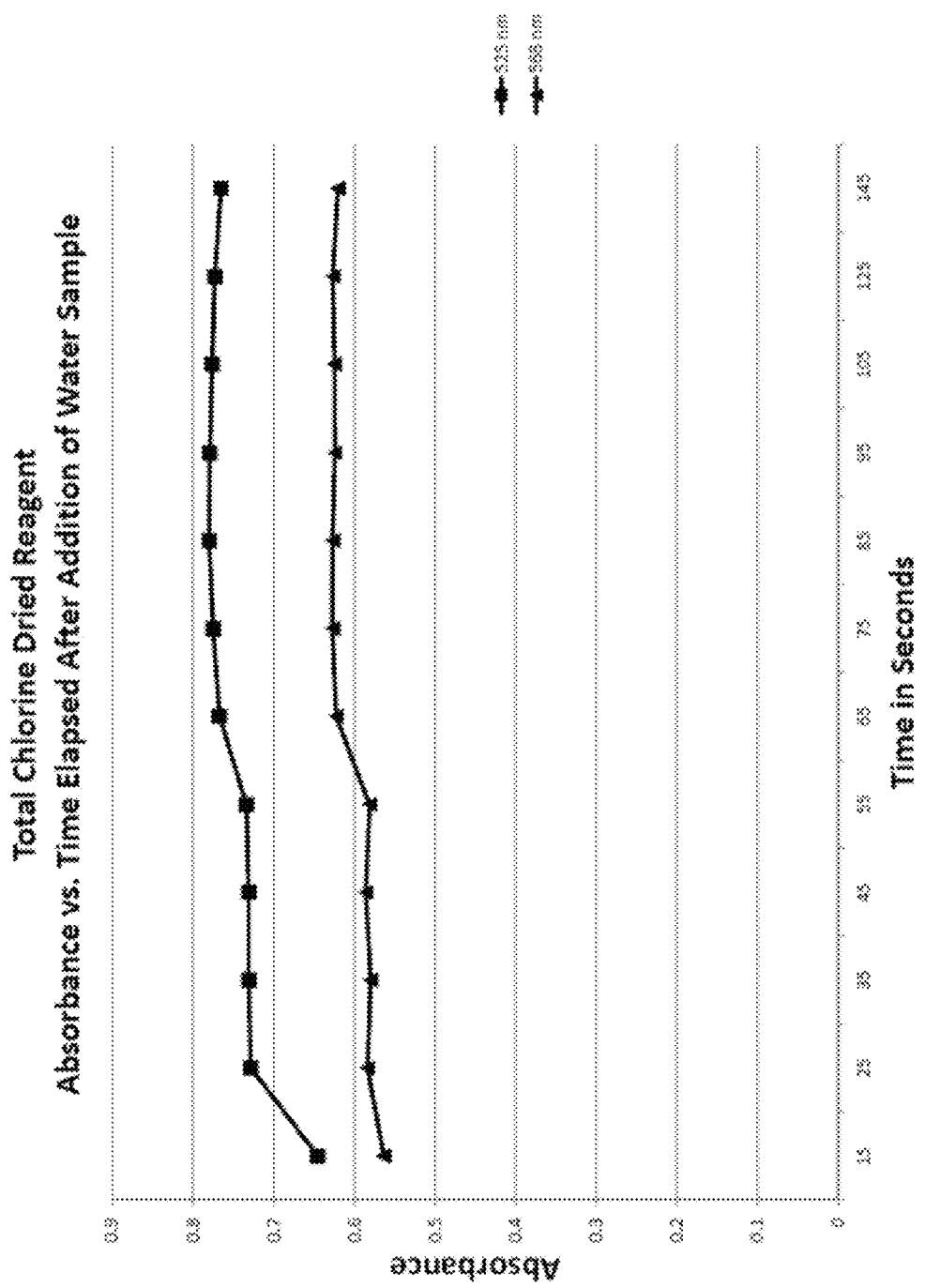
FIG. 2 depicts a graph of the absorbance at two different wavelengths as a function of time after rehydration of an exemplary heat dried reagent composition of the invention.

The assay reaction kinetics were studied using an exemplary heat dried reagent composition of the invention. The composition was hydrated with a volume of an aqueous sample comprising a known amount of free chlorine and the absorbance at either 525 nm or 568 nm was measured periodically. FIG. 2 depicts the resulting data.

The data show that the reaction reaches an absorbance plateau within 25 seconds at 525 nm. The plateau is sustained for about 30 seconds, then a slight increase of absorbance to a second plateau is observed. These data show that composition of the invention results in fast assay kinetics.

Example 3

Stability

To study the shelf life of heat dried reagent compositions, two reagent precursor compositions were prepared that differed only in the type of surfactant. The reagent precursor composition comprised: DPD, KI, EDTA, phosphate-borate buffer and either sodium ($C_{14}$-$C_{16}$) olefin sulfonate (purchased as BIO-TERGE® AS-40 from Stepan Company) or octyl phenol ethoxylate (purchased from J. T. Baker) as the surfactant.

The two reagent precursor compositions were aliquoted in 15 microliters into well strips and dried at 85° C. for 20 minutes. The strips were sealed in ZIPLOCK) foil bags that also contained 2 grams of desiccant. For the accelerated stability assays, the bags were placed in either a 38° C. incubator or a 55° C. incubator. For the shelf life stability experiment, the bag was stored on a shelf at room temperature.

Heat dried reagent compositions were tested on day 0 and then weeks 2, 4, 6, 8 and 12 for the accelerated stability study on the composition comprising sodium ($C_{14}$-$C_{16}$) olefin sulfonate; on day 0 and then weeks 2, 4, and 6 for the accelerated stability study on the composition comprising octyl phenol ethoxylate; and on day 0, month 6 and month 16 for the shelf life study on the composition comprising sodium ($C_{14}$-$C_{16}$) olefin sulfonate. Testing involved preparing four standard solutions containing 0 ppm. 0.5 ppm, 3 ppm and 8 ppm chlorine respectively. The standard solutions were prepared from sodium hypochlorite and CDF (chlorine demand free) water. Concentrations of the standards were verified using DPD SMART2 colorimetric method.

To perform the assay, 300 microliters of standard was added to a well containing a heat dried reagent composition and mixed by aspiration to rehydrate the composition. Absorbance was measured using SpectraMax 340PC Microplate Spectrophotometer at 530 nm. Assays were done in duplicate for each composition at each time point.

The accelerated stability study conditions are considered reasonably predictive for shelf life at room temperature as shown in Table 5.

TABLE 5

| | Equivalent shelf life Oven temperature | |
|---|---|---|
| Time in oven | 38° C. | 55° C. |
| 1 week | 2 months | 6 months |
| 2 weeks | 4 months | 1 year |
| 4 weeks | 8 months | 2 years |
| 8 weeks | 16 months | 4 years |
| 12 weeks | 2 years | 6 years |

Figure 3:
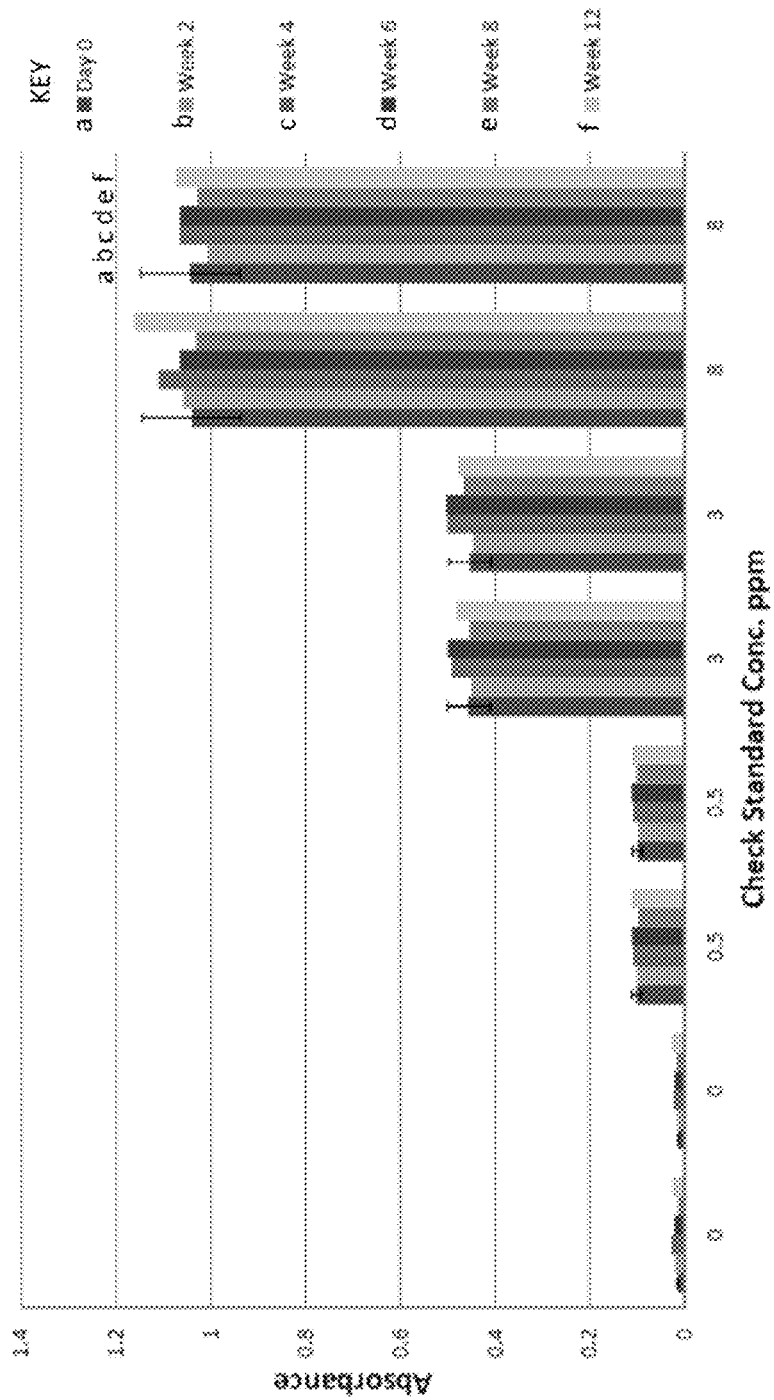
FIG. 3 depicts representative accelerated stability data for oven temperature of 38° C. for an exemplary heat dried reagent composition comprising sodium ($C_{14}$-$C_{16}$) olefin sulfonate. From left to right, the set of bars for each chlorine concentration depicted represent time points as follows: a: Day 0; b: Week 2; c: Week 4; d: Week 6; e: Week 8; and f: Week 12.
Figure 4:
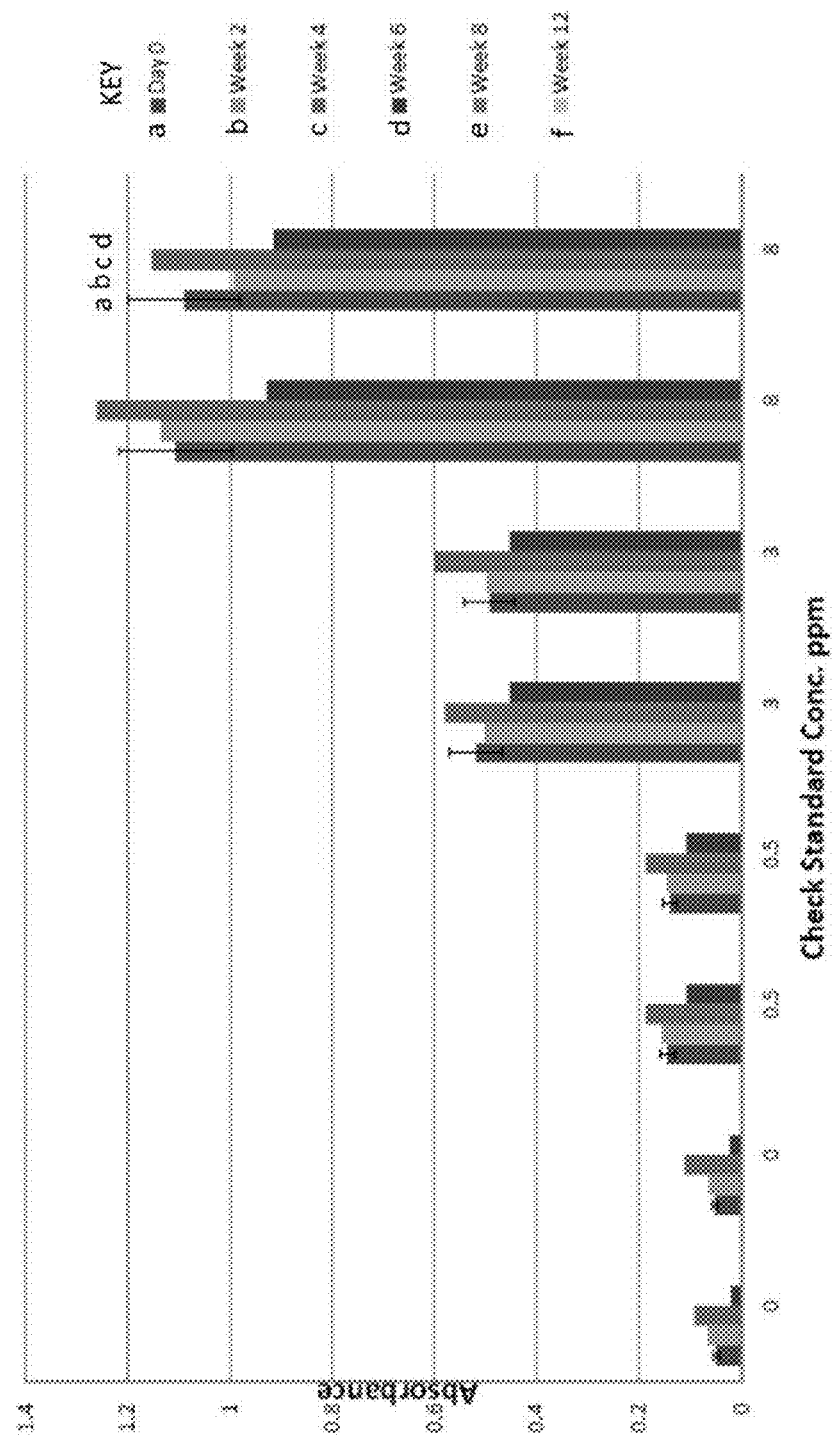
FIG. 4 depicts representative accelerated stability data for oven temperature of 38° C. for an exemplary heat dried reagent composition comprising octyl phenol ethoxylate. From left to right, the set of bars for each chlorine concentration depicted represent time points as follows: a: Day 0; b: Week 2; c: Week 4; and d: Week 6.

FIGS. 3 and 4 depict representative accelerated stability data for oven temperature of 38° C. for the heat dried reagent composition comprising sodium ($C_{14}$-$C_{16}$) olefin sulfonate and the heat dried reagent composition comprising octyl phenol ethoxylate, respectively.

The data in FIG. 3 demonstrate that the exemplary heat dried composition comprising sodium ($C_{14}$-$C_{16}$) olefin sulfonate was stable over the entire 12 weeks at 38° C. and at all amounts of chlorine tested. These data predict that the equivalent shelf life for the composition is at least about 2 years. The data in FIG. 4 demonstrate that the exemplary heat dried composition comprising octyl phenol ethoxylate also was stable over the entire 6 weeks at 38° C. and at all amounts of chlorine tested. These data predict that the equivalent shelf life for the composition comprising octyl phenol ethoxylate is at least greater than 8 months.

Figure 5:
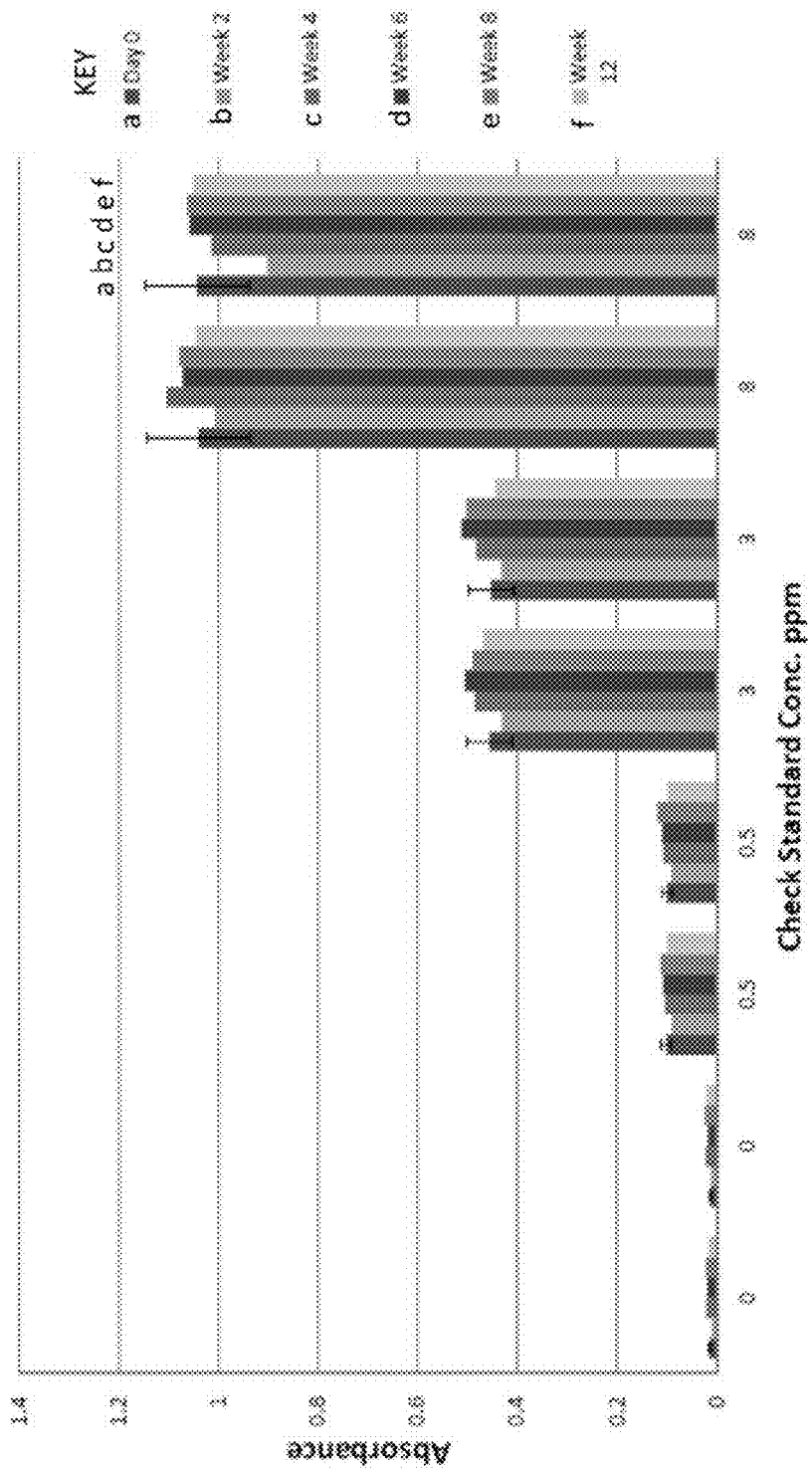
FIG. 5 depicts representative accelerated stability data for oven temperature of 55° C. for an exemplary heat dried reagent composition comprising sodium ($C_{14}$-$C_{16}$) olefin sulfonate. From left to right, the set of bars for each chlorine concentration depicted represent time points as follows: a: Day 0; b: Week 2; c: Week 4; d: Week 6; e: Week 8; and f: Week 12.
Figure 6:
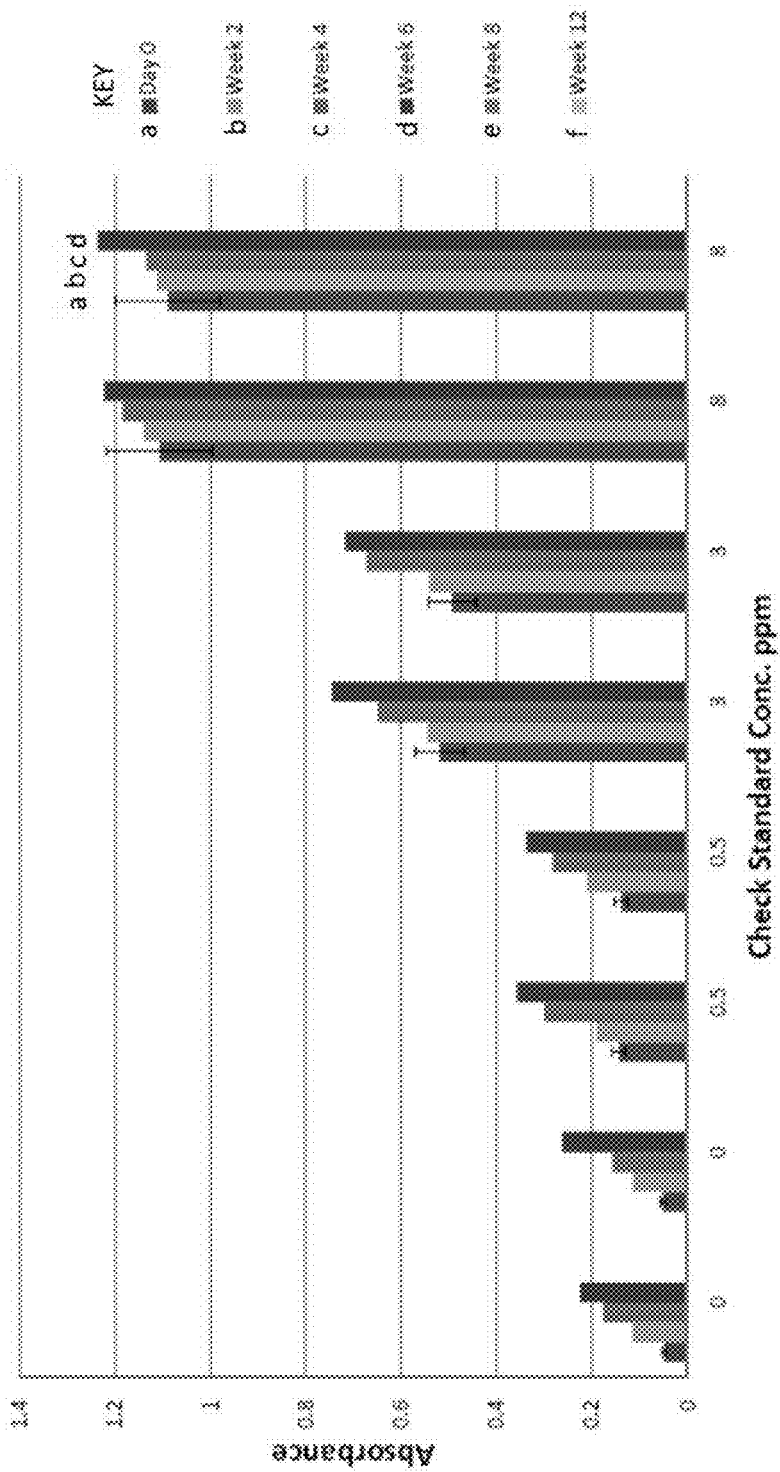
FIG. 6 depicts representative accelerated stability data for oven temperature of 55° C. for an exemplary heat dried reagent composition comprising octyl phenol ethoxylate. From left to right, the set of bars for each chlorine concentration depicted represent time points as follows: a: Day 0; b: Week 2; c: Week 4; and d: Week 6.

FIGS. 5 and 6 depict representative accelerated stability data for oven temperature of 55° C., for the heat dried reagent composition comprising sodium ($C_{14}$-$C_{16}$) olefin sulfonate and the heat dried reagent composition comprising octyl phenol ethoxylate, respectively.

The data in FIG. 5 demonstrate that the exemplary heat dried composition comprising sodium ($C_{14}$-$C_{16}$) olefin sulfonate was also stable over the entire 12 weeks at 55° C. and at all amounts of chlorine tested. These data predict that the equivalent shelf life for the composition is at least about 6 years. The data in FIG. 6 demonstrate that the exemplary heat dried composition comprising octyl phenol ethoxylate also was stable over the entire 6 weeks at 55° C. and at all amounts of chlorine tested. These data predict that the equivalent shelf life for the composition comprising octyl phenol ethoxylate is at least at least greater than 8 months.

FIG. 7 depicts representative shelf life data for the composition comprising sodium ($C_{14}$-$C_{16}$) olefin sulfonate. Consistent with the predicted shelf life based on the accelerated stability studies, the shelf life data illustrate that the exemplary heat dried reagent composition comprising sodium ($C_{14}$-$C_{16}$) olefin sulfonate has a stable shelf life of at least 16 months.

The disclosures of each and every patent, patent application, and publication cited herein are hereby incorporated herein by reference in their entirety.

While the products, methods of making them, and their methods of use have been disclosed with reference to specific embodiments, it is apparent that other embodiments and variations may be devised by others skilled in the art without departing from the true spirit and scope of the described products and methods. The appended claims are intended to be construed to include all such embodiments and equivalent variations.

What is claimed is:

1. A heat dried reagent composition for use in detecting and/or assessing total chlorine in an aqueous solution, the composition comprising:
   i) an indicator comprising N,N-diethyl-p-phenylenediamine (DPD) in an amount sufficient to detect and/or assess 0.01 to 20 parts per million (ppm) total chlorine in an aqueous reaction solution;
   ii) a source of iodide;
   iii) an anionic or nonionic surfactant;
   iv) ethylenediaminetetraacetic acid (EDTA); and
   v) a pH 6 buffer in an amount sufficient to obtain a pH of 3.5 to 7.5 in the aqueous reaction solution;
   wherein the composition is dry.

2. The heat dried reagent composition of claim 1, wherein the buffer is selected from the group consisting of: phosphate-borate; imidazole; bis-tris; citrate; malonic acid; malate; MES; and phosphate.

3. The heat dried reagent composition of claim 1, wherein the buffer is phosphate-borate.

4. The heat dried reagent composition of claim 1, wherein the surfactant comprises a surfactant selected from the group consisting of: sodium ($C_{14}$-$C_{16}$) olefin sulfonate; isopropylamine dodecylbenzene sulfonated, branched; sodium cholate; sodium dioctyl sulfosuccinate; sodium methyl oleoyl taurate; sodium polyoxyethylene(1) lauryl sulfate; octyl phenol ethoxylate; and any combination thereof.

5. The heat dried reagent composition of claim 1, wherein the surfactant comprises sodium ($C_{14}$-$C_{16}$) olefin sulfonate.

6. The heat dried reagent composition of claim 1, wherein the source of iodide is potassium iodide.

7. The heat dried reagent composition of claim 1, wherein:
   i) DPD in an amount that will result in 10 parts per million (ppm) to 1000 ppm in an aqueous reaction solution;
   ii) the source of iodide in an amount that will result in 200 ppm to 7000 ppm in the aqueous reaction solution;
   iii) the surfactant in an amount that will result in 30 ppm to 600 ppm in the aqueous reaction solution;
   iv) ethylenediaminetetraacetic acid (EDTA) in an amount that will result in 24 ppm to 960 ppm in the aqueous reaction solution; and
   v) the pH 6 buffer in an amount that will result in a 1 mM to 100 mM buffer concentration in the aqueous reaction solution.

8. A method of assessing total chlorine in an aqueous sample, comprising:
   combining an aqueous sample of interest with a heat dried reagent composition of claim 1 to form a reaction solution, measuring light absorbance of the reaction solution at a wavelength between 490 to 555 nanometers, and converting the light absorbance measurement to a total chlorine amount using a standard curve.

9. The method of claim 8, wherein the heat dried reagent composition is present in an analysis chamber of a device comprising at least one such chamber, and the aqueous sample of interest is introduced into the analysis chamber comprising the composition to form the reaction solution.

10. The method of claim 9, wherein the light absorbance is measured within 20 to 60 seconds after the formation of the reaction solution.

11. The method of claim 10, wherein the light absorbance is measured at a wavelength between 490 nm to 530 nm.

12. The method of claim 9, wherein the aqueous sample of interest is added to the heat dried reagent composition to form the reaction solution having a final volume of 40 microliters to 1 milliliter.

13. A method of detecting total chlorine in an aqueous sample, comprising:
   combining an aqueous sample of interest with a heat dried reagent composition of claim 1 to form a reaction solution, and
   observing the color of the reaction solution,
wherein a pink color in the reaction solution is indicative of total chlorine in the aqueous sample of interest.

14. A method of preparing a heat dried reagent composition for use in detecting and/or assessing total chlorine in an aqueous solution, the method comprising:
   drying a volume of an aqueous reagent precursor solution comprising:
      i) an indicator comprising N,N-diethyl-p-phenylenediamine (DPD) in an amount sufficient to detect and/or assess 0.01 to 20 parts per million (ppm) total chlorine in an aqueous reaction solution;
      ii) a source of iodide;
      iii) a pH 6 buffer in an amount sufficient to obtain a pH of 3.5 to 7.5 in the aqueous reaction solution;
      iv) an anionic or nonionic surfactant;
      and
      v) ethylenediaminetetraacetic acid (EDTA);
   wherein the drying is performed at a temperature from about 50° C. to about 105° C. for a sufficient time to obtain a dry composition.

15. The method of claim 14, wherein the volume of the aqueous reagent precursor solution is from about 5 microliters to about 150 microliters.

16. The method of claim 15, wherein the drying is performed at a temperature from about 70° C. to about 95° C.

17. The method of claim 16, wherein the volume of the aqueous reagent precursor solution is from about 5 microliters to about 50 microliters.

18. The method of claim 14, further comprising, prior to the drying step, the step of aliquoting the aqueous reagent precursor solution into an analysis chamber of a device comprising as least one such chamber.

19. The method of claim 14, wherein the heat dried reagent composition comprises:
   i) DPD in an amount that will result in 10 parts per million (ppm) to 1000 ppm in an aqueous reaction solution;
   ii) the source of iodide in an amount that will result in 200 ppm to 7000 ppm in the aqueous reaction solution;
   iii) the surfactant in an amount that will result in 30 ppm to 600 ppm in the aqueous reaction solution;
   iv) ethylenediaminetetraacetic acid (EDTA) in an amount that will result in 24 ppm to 960 ppm in the aqueous reaction solution;
   and
   v) the pH 6 buffer in an amount that will result in a 1 mM to 100 mM buffer concentration in the aqueous reaction solution.

20. The method of claim 19, wherein the aqueous reagent precursor solution is about 5 to 30 fold more concentrated than the concentration of the aqueous reaction solution.

* * * * *